United States Patent [19]
Van Niel et al.

[11] Patent Number: 5,495,047
[45] Date of Patent: Feb. 27, 1996

[54] FUSED TRICYCLIC COMPOUNDS, PHARMACEUTICAL COMPOSITIONS CONTAINING THEM AND THEIR USE IN THERAPY

[75] Inventors: Monique B. Van Niel, Welwyn Garden City; Brian J. Williams, Great Dunmow, both of United Kingdom; Walfred S. Saari, Lansdale, Pa.

[73] Assignee: Merck, Sharp & Dohme (Ltd.), Hoddesdon, England

[21] Appl. No.: 175,432

[22] PCT Filed: Jul. 3, 1992

[86] PCT No.: PCT/GB92/01212

§ 371 Date: Apr. 21, 1994

§ 102(e) Date: Apr. 21, 1994

[87] PCT Pub. No.: WO93/01159

PCT Pub. Date: Jan. 21, 1993

[30] Foreign Application Priority Data

Jul. 10, 1991 [GB] United Kingdom ............... 9114886
Apr. 14, 1992 [GB] United Kingdom ............... 9208141

[51] Int. Cl.⁶ ............... C07C 217/48; A61K 31/135

[52] U.S. Cl. ............... 564/346; 560/38; 560/39; 560/41; 564/165; 564/219

[58] Field of Search ............... 564/165, 219, 564/346; 514/620, 538, 630, 651; 560/38, 39, 41

[56] References Cited

FOREIGN PATENT DOCUMENTS

| 0394989A3 | 10/1990 | European Pat. Off. . |
| 2035535 | 1/1971 | Germany . |
| 2054588 | 2/1981 | United Kingdom . |

OTHER PUBLICATIONS

March, "Advanced Organic Chemistry," 3rd ed., John Wiley & Sons, New York (1985), p. 342.

Chem. Abstracts, vol. 64, 1966, No. 8294b.

Primary Examiner—José G. Dees
Assistant Examiner—Barbara S. Frazier
Attorney, Agent, or Firm—Robert J. North; Melvin Winokur

[57] ABSTRACT

Fused tricyclic compounds of formula (I) as disclosed herein, and salts and prodrugs thereof, are tachykinin antagonists, useful for treating pain.

12 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Arg Pro Lys Pro Gln Gln Phe Phe Gly Leu Met
1               5                           10

( 2 ) INFORMATION FOR SEQ ID NO:2:

( i ) SEQUENCE CHARACTERISTICS:
( A ) LENGTH: 10 amino acids
( B ) TYPE: amino acid
( C ) STRANDEDNESS: single (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:2:

His Lys Thr Asp Ser Phe Val Gly Leu Met
1               5                   10

(2) INFORMATION FOR SEQ ID NO:3:

(i) SEQUENCE CHARACTERISTICS:
    (A) LENGTH: 10 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (xi) SEQUENCE DESCRIPTION: SEQ ID NO:3:

Asp Met His Asp Phe Phe Val Gly Leu Met
1               5                   10

FUSED TRICYCLIC COMPOUNDS, PHARMACEUTICAL COMPOSITIONS CONTAINING THEM AND THEIR USE IN THERAPY

This application is a 371 of PCT/GB92/01212, filed Jul. 3, 1992.

This invention relates to a class of tricyclic compounds, which are useful as tachykinin receptor antagonists.

The tachykinins are a group of naturally-occurring peptides found widely distributed throughout mammalian tissues, both within the central nervous system and in the peripheral nervous and circulatory systems. The structures of three known mammalian tachykinins are as follows:

Substance P:
Arg-Pro-Lys-Pro-Gln-Gln-Phe-Phe-Gly-Leu-Met-NH$_2$ SEQ ID NO.1

Neurokinin A:
His-Lys-Thr-Asp-Ser-Phe-Val-Gly-Leu-Met-NH$_2$ SEQ ID NO.2

Neurokinin B:
Asp-Met-His-Asp-Phe-Phe-Val-Gly-Leu-Met-NH$_2$ SEQ ID NO.3

Substance P is believed inter alia to be involved in the neurotransmission of pain sensations [Otsuka et al, "Role of Substance P as a Sensory Transmitter in Spinal Cord and Sympathetic Ganglia" in 1982 Substance P in the Nervous System, Ciba Foundation Symposium 91, 13–34 (published by Pitman) and Otsuka and Yanagisawa, "Does Substance P Act as a Pain Transmitter?" TIPS (Dec. 1987) 8 506–510], specifically in the transmission of pain in migraine (B. E. B. Sandberg et al, J. Med Chem, (1982) 25 1009) and in arthritis [Levine et al in Science (1984) 226 547–549]. These peptides have also been implicated in gastrointestinal (GI) disorders and diseases of the GI tract such as inflammatory bowel disease [Mantyh et al in Neuroscience (1988) 25 (3) 817– 37 and D. Regoli in "Trends in Cluster Headache" Ed. Sicuteri et al Elsevier Scientific Publishers, Amsterdam (1987) page 85)]. It is also hypothesised that there is a neurogenic mechanism for arthritis in which substance P may play a role [Kidd et al "A Neurogenic Mechanism for Symmetrical Arthritis" in The Lancet, 11 Nov. 1989 and Grönblad et al "Neuropeptides in Synovium of Patients with Rheumatoid Arthritis and Osteoarthritis" in J. Rheumatol. (1988) 15(12) 1807–10]. Therefore, substance P is believed to be involved in the inflammatory response in diseases such as rheumatoid arthritis and osteoarthritis [O'Byrne et al in Arthritis and Rheumatism (1990) 33 1023–8]. Other disease areas where tachykinin antagonists are believed to be useful are allergic conditions [Hamelet et al Can. J. Pharmacol. Physiol. (1988) 66 1361–7], immunoregulation [Lotz et al Science (1988) 241 1218–21 and Kimball et al, J. Immunol. (1988) 141 (10) 3564–9], vasodilation, bronchospasm, reflex or neuronal control of the viscera [Mantyh et al, PNAS (1988) 85 3235–9] and, possibly by arresting or slowing β-amyloid-mediated neurodegenerative changes [Yankner et al, Science (1990) 250, 279–82], in senile dementia of the Alzheimer type, Alzheimer's disease and Down's Syndrome. Substance P may also play a role in demyelinating diseases such as multiple sclerosis and amyotrophic lateral sclerosis [J. Luber-Narod et. al., poster to be presented at C.I.N.P. XVIIIth Congress, 28th June-2nd July, 1992, in press], and in disorders of bladder function such as bladder detrusor hyper-reflexia (Lancet, 16th May, 1992, 1239).

It has furthermore been suggested that tachykinins have utility in the following disorders: depression, dysthymic disorders, chronic obstructive airways disease, hypersensitivity disorders such as poison ivy, vasospastic diseases such as angina and Reynauld's disease, fibrosing and collagen diseases such as scleroderma and eosinophillic fascioliasis, reflex sympathetic dystrophy such as shoulder/hand syndrome, addiction disorders such as alcoholism, stress related somatic disorders, neuropathy, neuralgia, disorders related to immune enhancement or suppression such as systemic lupus erythromatosis (European patent application no. 0 436 334), opthalmic disease such as conjuctivitis, vernal conjunctivitis, and the like, and cutaneous diseases such as contact dermatitis, atropic dermatitis, urticaria, and other eczematoid dermatitis (European patent application no. 0 394 989).

In view of their metabolic instability, peptide derivatives are likely to be of limited utility as therapeutic agents. It is for this reason that non-peptide tachykinin receptor antagonists are sought.

In essence, this invention provides a class of potent non-peptide tachykinin receptor antagonists. By virtue of their non-peptide nature, the compounds of the present invention do not suffer from the shortcomings, in terms of metabolic instability, of known peptide-based tachykinin receptor antagonists.

The present invention provides a compound of formula (I), or a salt or prodrug thereof:

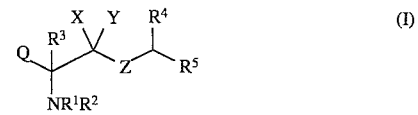

wherein

Q represents a group

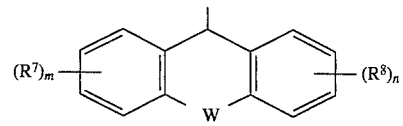

where W represents a bond, O, S, —CH$_2$CH$_2$—, —CH=CH— or a group NR$^6$, where R$^6$ is H or C$_{1-6}$alkyl and one or both of the phenyl rings may be replaced by a heteroaryl moiety;

X and Y each represent H or X and Y together form a group =O;

Z represents O, S or NR$^8$, where R$^8$ represents H or C$_{1-6}$alkyl;

R$^1$ and R$^2$ independently represent H; C$_{1-6}$ alkyl optionally substituted by hydroxy, cyano, COR$^a$, COOR$^a$, CONR$^a$R$^b$, COC$_{1-4}$alkylNR$^a$R$^b$, CONR$^a$C$_{1-4}$alkylCONR$^a$R$^b$ or NR$^a$R$^b$, (where R$^a$ and R$^b$ each independently represent H, C$_{1-6}$ alkyl, phenyl (optionally substituted by one or more of C$_{1-6}$alkyl, C$_{1-6}$alkoxy, halo and trifluoromethyl) or phenyl(C$_{1-4}$alkyl) (optionally substituted in the phenyl ring by one or more of C$_{1-6}$ alkyl, C$_{1-6}$ alkoxy, halo and trifluoromethyl)); phenyl(C$_{1-4}$ alkyl), (optionally substituted by one or more of C$_{1-6}$ alkyl, C$_{1-6}$ alkoxy, halo and trifluoromethyl in the phenyl ring); C$_{2-6}$ alkylene; COC$_{1-6}$alkylhalo; COR$^a$; COOR$^a$; CONHR$^a$; COC$_{1-4}$alkylNR$^a$R$^b$; or CONR$^a$C$_{1-4}$alkylCONR$^a$R$^b$; (where R$^a$ and R$^b$ are as previously defined) or R$^1$ and R$^2$ together form a chain (CH$_2$)$_p$ where p is 4 or 5 and where one non-terminal methylene group may optionally be replaced by an oxygen atom or a group NR$^x$, where R$^x$ is H or C$_{1-6}$ alkyl;

R$^3$ represents H or C$_{1-6}$alkyl;

$R^4$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ each independently represent H, $C_{1-6}$ alkyl, phenyl or trifluoromethyl);

$R^5$ represents $(CH_2)_q$phenyl, wherein q is 0, 1, 2 or 3 which may optionally be substituted in the phenyl ring by one or more of $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined;

each $R^7$ and $R^8$ independently represents $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined; and m and n independently represent 0, 1, 2, 3 or 4.

The alkyl, alkenyl and alkynyl groups referred to with respect to any of the above formulae may represent straight, branched or cyclic groups. Thus, for example, suitable alkyl groups include methyl, ethyl, n- or iso-propyl, n-, sec-, iso- or tert-butyl, cyclopropyl, cyclobutyl, cyclopentyl or cyclohexyl, and cycloalkylalkyl groups such as cyclopropylmethyl; suitable alkenyl groups include vinyl are allyl; and suitable alkynyl groups include propargyl.

The term "halo" as used herein includes fluoro, chloro, bromo and iodo, especially chloro and fluoro.

When one or both of the phenyl rings of Q is/are replaced by a heteroaryl moiety, this will suitably be a pyridyl moiety.

A particular subgroup of compounds according to formula (I) is represented by compounds wherein Q represents a group

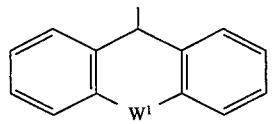

where $W^1$ is a bond, O, S or a group $NR^6$, where $R^6$ is H or $C_{1-6}$ alkyl;

$R^1$ and $R^2$ each independently represent H, $C_{1-6}$ alkyl, phenyl($C_{1-4}$ alkyl), $COR^{10}$, $COOR^{10}$ or $CONHR^{10}$, where $R^{10}$ is $C_{1-6}$ alkyl or phenyl;

$R^4$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, $SCH_3$, $SOCH_3$, $SO_2CH_3$, $OR^c$, $NR^cR^d$, $NR^cCOR^d$, $NR^cCOOR^d$, $COOR^c$ or $CONR^cR^d$ (where $R^c$ and $R^d$ are as above defined); and $R^5$ represents $(CH_2)_q$phenyl, wherein q is 0, 1, 2 or 3 which may optionally be substituted in the phenyl ring by one or more of $C_{1-6}$ alkyl, $C_{2-6}$ alkenyl, $C_{2-6}$ alkynyl, halo, cyano, nitro, trifluoromethyl, $SCH_3$, $SOCH_3$, $SO_2CH_3$, $OR^c$, $NR^cR^d$, $NR^cCOR^d$, $NR^cCOOR^d$, $COOR^c$ or $CONR^cR^d$ (where $R^c$ and $R^d$ are as above defined);

wherein any phenyl (including benzyl) ring in the definitions of $R^1$ or $R^2$ (including $R^{10}$) above may be optionally substituted by one or more of $C_{1-6}$ alkyl, $C_{1-6}$ alkoxy, halo or trifluoromethyl.

In the compounds of the invention, W suitably represents a bond, $CH_2CH_2$ or $HC=CH$.

Preferably Q is 10,11-dihydro-5H-dibenzo[a,d] cyclohepten-5-yl, 5H-dibenzo[a,d]cyclohepten-5-yl or 9-fluorenyl.

Preferably X and Y each represent H.

Preferably Z represents oxa.

Suitable values for the groups $R^1$ and $R^2$ include H, $C_{1-6}$ alkyl, especially methyl; $C_{1-6}$alkyl substituted by, for example, cyano, hydroxy, $NH_2$, $CO_2C_{1-6}$alkyl and $CONH_2$.

Suitable values for the group $R^3$ include H and methyl, preferably H.

Preferably $R^4$ represents H.

Suitably $R^5$ represents $(CH_2)_q$phenyl where q is 0, 1 or 2 and the phenyl is substituted. Suitable phenyl substituents include methyl, methoxy, nitro, cyano, halo and trifluoromethyl. Preferably $R^5$ represents a substituted phenyl group. More preferably $R^5$ represents 3,5-dimethylphenyl or 3,5-bistrifluoromethylphenyl.

Preferably m and n each represent O.

A preferred sub-group of compounds according to the invention is represented by formula (Ia)

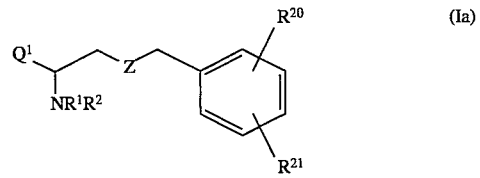

wherein $R^1$, $R^2$ and Z are as defined for formula (I) above;

$Q^1$ represents 10,11-dihydro-5H-dibenzo[a,d] cyclohepten-5-yl, 5H-dibenzo[a,d]cylcohepten-5-yl or 9-fluorenyl.

$R^{20}$ and $R^{21}$ each independently represent H, $C_{1-6}$ alkyl, $C_{2-6}$ alkenyl, $C_{2-6}$ alkynyl, halo, cyano, nitro, trifluoromethyl, trimethylsilyl, $SR^c$, $SOR^c$, $SO_2R^c$, $OR^c$, $NR^cR^d$, $NR^cCOR^d$, $NR^cCOOR^d$, $COOR^c$ or $CONR^cR^d$, where $R^c$ and $R^d$ are as above defined; and salts and prodrugs thereof.

Particularly preferred are compounds of formula (Ia) wherein $R^{20}$ and $R^{21}$ are other than hydrogen and are located in the 3- and 5-positions. Most preferably $R^{20}$ and $R^{21}$ each represent methyl or trifluoromethyl.

For use in medicine, the salts of the compounds of formula I will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, oxalic acid, fumaric acid, p-toluenesulphonic acid, maleic acid, succinic acid, acetic acid, citric acid, tartaric acid, carbonic acid or phosphoric acid. Salts of amine groups may also comprise quaternary ammonium salts in which the amino nitrogen atom carries a suitable organic group such as an alkyl, alkenyl, alkynyl or aralkyl moiety. Thus, for example, when both $R^1$ and $R^2$ are other than hydrogen, the nitrogen atom to which they are attached may be further substituted to give a quaternary ammonium salt. Furthermore, where the compounds of the invention carry an acidic moiety, suitable pharmaceutically acceptable salts thereof may, include metal salts such as alkali metal salts, e.g. sodium or potassium salts; and alkaline earth metal salts, e.g. calcium or magnesium salts.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

The compounds according to the invention may exist both as enantiomers and as diastereomers. It is to be understood that all such isomers and mixtures thereof are encompassed within the scope of the present invention.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

The present invention further provides a process for preparing a pharmaceutical composition comprising a compound of formula (I), which process comprises bringing a compound of formula (I) into association with a pharmaceutically acceptable carrier or excipient.

The compounds of the present invention are of value in the treatment of a wide variety of clinical conditions which are characterised by the presence of an excess of tachykinin, in particular substance P, activity. These may include disorders of the central nervous system such as anxiety, depression, psychosis and schizophrenia; neurodegenerative disorders such as dementia, including senile dementia of the Alzheimer type, Alzheimer's disease and Down's syndrome; demyelinating diseases such as MS and ALS and other neuropathological disorders such as peripheral neuropathy, for example, diabetic or chemotherapy-induced neuropathy, and postherpetic and other neuralgias; respiratory diseases such as chronic obstrucutive airways disease, bronchopneumonia, bronchospasm and asthma; inflammatory diseases such as inflammatory bowel disease, psoriasis, fibrositis, osteoarthritis and rheumatoid arthritis; allergies such as eczema and rhinitis; hypersensitivity disorders such as poison ivy; ophthalmic diseases such as conjunctivitis, vernal conjunctivitis, and the like; cutaneous diseases such as contact dermatitis, atropic dermatitis, urticaria, and other eczematoid dermatitis; addiction disorders such as alcoholism; stress related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal (GI) disorders and diseases of the GI tract such as disorders associated with the neuronal control of viscera such as ulcerative colitis, Crohn's disease and incontinence; disorders of bladder function such as bladder detrusor hyper-reflexia; fibrosing and collagen diseases such as scleroderma and eosinophilic fascioliasis; disorders of blood flow caused by vasodilation and vasospastic diseases such as angina, migraine and Reynaud's disease; and pain or nociception, for example, that attributable to or associated with any of the foregoing conditions, especially the transmission of pain in migraine. For example, the compounds of formula (I) may suitably be used in the treatment of disorders of the central nervous system such as anxiety, psychosis and schizophrenia; neurodegenerative disorders such as senile dementia of the Alzheimer type, Alzheimer's disease and Down's syndrome; respiratory diseases such as bronchospasm and asthma; inflammatory diseases such as inflammatory bowel disease, osteoarthritis and rheumatoid arthritis; adverse immunological reactions such as rejection of transplanted tissues; gastrointestinal (GI) disorders and diseases of the GI tract such as disorders associated with the neuronal control of viscera such as ulcerative colitis, Crohn's disease and incontinence; disorders of blood flow caused by vasodilation; and pain or nociception, for example, that attributable to or associated with any of the foregoing conditions or the transmission of pain in migraine.

The compounds of formula (I) are particularly useful in the treatment of pain or nociception and/or inflammation and disorders associated therewith such as, for example, neuropathy, such as diabetic and chemotherapy-induced neuropathy, postherpetic and other neuralgias, asthma, osteoarthritis, rheumatoid arthritis and migraine.

The present invention further provides a compound of formula (I) for use in the manufacture of a medicament for the treatment of physiological disorders associated with an excess of tachykinins, especially substance P. The present invention also provides a method for the the treatment or prevention of physiological disorders associated with an excess of tachykinins, especially substance P, which method comprises administration to a patient in need thereof of a tachykinin reducing amount of a compound or composition of this invention.

In the treatment of conditions involving actions of tachykinins released physiologically in response to noxious or other stimuli, a suitable dosage level is about 0.001 to 50 mg/kg per day, such as 0.001 to 25 mg/kg per day, preferably about 0.005 to 10 mg/kg per day, and especially about 0.005 to 5 mg/kg per day. The compounds may be administered on a regimen of 1 to 4 times per day, preferably once daily.

The compounds according to the invention wherein Z is O or S may be prepared by reaction of a compound of formula (II)

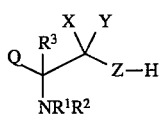

wherein Q, $R^1$, $R^2$, $R^3$, X and Y, are defined as for formula (I) and Z is O or S, with a compound of formula HalCHR$^4$R$^5$, where $R^4$ and $R^5$ are as defined for formula (I) and Hal is halo, such as bromo, chloro or iodo, in the presence of a base.

The reaction is conveniently carried out in a suitable organic solvent, such as an ether, for example, tetrahydrofuran.

Suitable bases of use in the reaction include alkali or alkaline earth metal hydrides, for example, sodium hydride.

The compounds of formula (I) prepared to the above described process may, if necessary or desired be converted to other compounds of formula (I). Thus, for example, the compounds of the invention wherein Z is a group $NR^8$ and X and Y together represent =O may be prepared from the compounds of formula (II) wherein Z is O and X and Y together represent =O by reaction with a compound of formula HNR$^8$CHR$^4$R$^5$ in the presence of a coupling agent, such as dicyclohexylcarbodiimide.

The reaction is conveniently effected in a suitable organic solvent, such as an ether, for example, diethyl ether or tetrahydrofuran.

The compounds according to the invention wherein Z is $NR^8$ and X and Y are hydrogen may be prepared from the corresponding compounds of formula (I) wherein X and Y together represent =O, by reduction.

Suitable reducing agents of use in the reaction include borane and metal hydrides, such as lithium aluminium hydride. The reaction is conveniently effected in a suitable organic solvent, such as an ether, for example, tetrahydrofuran.

Compounds of formula (II) wherein Z is O and X and Y together represent a group =O may be prepared, for example, from intermediates of formula (III)

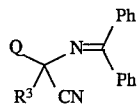

wherein Q and $R^3$ are as above defined and Ph represents phenyl, by hydrolysis.

The reaction is conveniently effected by heating a solution of the compound of formula (III) in concentrated hydrochloric acid at reflux.

Alternatively, compounds of formula (II) wherein Z is O, X and Y are =O and $R^3$ is H may be prepared from intermediates of formula (IVA)

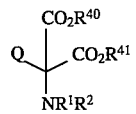

wherein Q, $R^1$ and $R^2$ are as above defined, and $R^{40}$ and $R^{41}$ both represent H (IRA), by decarboxylation.

The reaction is conveniently effected by heating the compound of formula (IVA) in a concentrated mineral acid, such as concentrated hydrochloric acid, to a temperature of about 90°–120° C., such as about 100° C.

Compounds of formula (II) wherein Z is O and X and Y are =O may also be prepared by conventional procedures for the preparation of amino acids which are well documented and are described, for example, in Chemistry and Biochemistry of the Amino Acids, ed. G. C. Barrett, Chapman and Hall, 1985.

Compounds of formula (II) wherein Z is S may be prepared from the corresponding compounds of formula (II) wherein Z is O by treating the latter compound with Lawesson's reagent or phosphorus pentasulphide in a suitable solvent, e.g. pyridine, at ambient or elevated temperature, suitably at the reflux temperature of the chosen solvent.

Compounds of formula (II) wherein X and Y represent H may be prepared from the corresponding compounds of formula (II) wherein X and Y together represent =O, by reduction.

Suitable reducing agents include metal hydrides, such as lithium aluminium hydride. The reaction is conveniently effected in a suitable organic solvent, such as an ether, for example, tetrahydrofuran, suitably at elevated temperature, such as the reflux temperature of the solvent.

Intermediates of formula (III) may be prepared from compounds of formula (V)

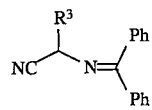

wherein $R^3$ is as defined for formula (I), by reaction with a compound of formula Q-Hal wherein Hal is halo, such as bromo, chloro or iodo, in the presence of a base.

Suitable bases of use in the reaction include metal hydroxides, for example, sodium hydroxide. The reaction is conveniently effected in a mixture of water and a suitable organic solvent, such as a hydrocarbon, for example, toluene, in the presence of a phase transfer catalyst, such as benzyltrimethyl ammonium chloride.

Compounds of formula (V) are commercially available or may be prepared by procedures readily apparent to one skilled in the art.

Compounds of formula (IVA) may be prepared from the corresponding compounds of formula (IV) wherein $R^{40}$ and $R^{41}$ each represent alkyl (IVB), by saponification.

The saponification is conveniently effected using an alkali metal hydroxide, such as sodium hydroxide, in an aqueous solvent, such as aqueous alcohol, for example, aqueous methanol, preferably at elevated temperature, e.g. the reflux temperature of the chosen solvent.

Compounds of formula (IVB) may be prepared by reaction of a compound of formula Q-Hal as above defined with a malonate derivative of formula $R^{41}O_2CCH(NR^1R^2)CO_2R^{40}$, which malonate derivatives are commercially available or may be prepared from commercially available compounds by conventional means known to those skilled in the art.

Compounds of formula Q-Hal are commercially available or may be prepared by conventional procedures known to those skilled in the art.

Compounds of formula (I) may also be prepared from other compounds of formula (I). Thus, for example, compounds of formula (I) wherein one or both of $R^1$ and $R^2$ represent hydrogen may be reacted with an optionally substituted alkylating or an acylating agent to produce compounds of formula (I) wherein one or both of $R^1$ and $R^2$ represent an optionally substituted alkyl or an acyl group. Suitable procedures are described in the accompanying examples, or will be readily apparent to one skilled in the art.

Conversely, compounds of formula (I) wherein one or both of $R^1$ and $R^2$ represent, for example, an acyl or a benzyl group, may be converted to compounds of formula (I) wherein one or both of $R^1$ and $R^2$ represent H by, for example, hydrolysis or catalytic hydrogenation. Suitable reagents and conditions are described in the accompanying examples, or will be readily apparent to one skilled in the art of organic chemistry.

Intermediates of formula (II) are novel compounds. Intermediates of formula (II) and the preparation thereof represent further aspects of the present invention.

Where the above-described process for the preparation of the compounds according to the invention gives rise to mixtures of stereoisomers these isomers may, if desired, be separated, suitably by conventional techniques such as preparative chromatography.

The novel compounds may be prepared in racemic form, or individual enantiomers may be prepared either by enantiospecific synthesis or by resolution. The novel compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wutts, *Protective Groups in Organic Synthesis*, John Wiley & Sons, 1991. The protecting groups may be removed at a convenient subsequent stage using methods known from the art.

The following Examples illustrate the preparation of compounds according to the invention.

EXAMPLE 1

1-(5H-Dibenzo[a,d]cyclohepten-5-yl)-2-(3,5-dimethylbenzyloxy)ethylamine, oxalate salt a) Through a cooled (−15° C.) solution of dibenzosuberenol (20g) and calcium chloride (20g) in toluene (750ml) was bubbled hydrogen chloride gas for 15 minutes. The solution was warmed to room temperature over 1 hour and hydrogen chloride gas bubbled through for a further 20 minutes. After 16 hours the solution was filtered and the filtrate evaporated in vacuo to leave 5-chloro-5H-dibenzo [a,d]cycloheptene as a yellow crystalline solid. $^1$H NMR (360MHz, CDCl$_3$) δ 6.25 (1H, bs), 7.14 (2H, s), 7.39–7.45 (8H, m).

b) To a stirred suspension of diethyl acetamidomalonate (21.2g) in tetrahydrofuran (150ml) was slowly added sodium hydride (3.4g, 80% dispersion in oil) under an atmosphere of nitrogen. After 1h to this solution was added a solution of 5-chloro-5H-dibenzo[a,d]cycloheptene (20.3g, Example 1a) in tetrahydrofuran (100ml). The solution was heated to reflux for 18h, cooled to room temperature and to this was added a saturated solution of NH$_4$Cl and ethyl acetate. The organic phase was dried (MgSO$_4$), concentrated in vacuo and the residue chromatographed on silica (eluting with ethyl acetate:petroleum ether bp 60°–80° C. (1:4). This gave diethyl(5H-dibenzo[ a,d]cyclohepten-5-yl)-2-acetamidomalonate as a yellow solid. $^1$H NMR (360MHz, CDCl$_3$) δ 1.02–1.04 (6H, m), 1.6 (3H, s), 3.82–3.91 (2H, m), 4.0–4.13 (2H, m), 5.78 (1H, s), 6.39 (1H, s), 6.79 (2H, s), 7.21–7.36 (6H, m), 7.54–7.56 (2H, m).

c) A mixture of diethyl 2-(5H-dibenzo[a,d]cyclohepten-5-yl)- 2-acetamidomalonate (20.2g, Example 1b) and sodium hydroxide (4g) in methanol (75ml) and water (75ml) was heated to reflux for 8h. To the cooled solution was added 1M-HCl until pH=6. The solution was concentrated in vacuo and acidified to pH=2 by addition of 1M-HCl. The solid which formed was collected by filtration and heated together with 6M-HCl for 3h at 100° C. The cooled solution was filtered and the residue dissolved in hot water, refiltered and to the filtrate was added aqueous ammonia until pH 7–8. The solid which formed on cooling to room temperature was collected by filtration and dried in vacuo to give 5H-dibenzo [a,d]cyclohepten-5-ylglycine. $^1$H NMR (360MHz, d$_4$ MeOH), δ 4.08–4.12 (1H, m), 4.35–4.39 (1H, m), 7.0–7.11 (2H, m), 7.24–7.30 (3H, m), 7.34–7.45 (5H, m).

d) 5-H-Dibenzo[a,d]cyclohepten-5-ylglycine (4.8g, Example 1c) was added in portions to a solution of lithium aluminium hydride (54ml of 1.0M solution) in 30ml dry THF at 0° C. The reaction was allowed to stand at room temperature overnight, quenched with 2N sodium hydroxide and poured through Celite. The filtrate was washed with water, dried over MgSO$_4$ and solvent removed in vacuo to leave a residue which was induced to crystallised in ethyl acetate or dichloromethane to give 5H-dibenzo[ a,d]cycloheptene glycinol. $^1$H NMR (360MHz, d$_4$ MeOH) δ 3.05–3.17 (2H, m), 3.29–3.33 (1H, m), 3.89–3.94 (1H, m), 6.90–6.97 (2H, m), 7.23–7.38 (8H, m).

e) A mixture of 5H-dibenzo[a,d]cycloheptene glycinol (1.13g, Example 1d) and di-tert-butyldicarbonate (1.0g) in 10ml CH$_2$Cl$_2$ was stirred at room temperature for 1.5h. Solvent was removed in vacuo to give N-tert-butoxycarbonyl (5H-dibenzo[ a,d]cycloheptene) glycinol which could be induced to crystallise in diethyl ether. $^1$H NMR (360MHz, CDCl$_3$) δ 1.24 (9H, s), 2.43 (1H, brs), 3.1–3.3 (1H, m), 3.3–3.5 (1H, m), 4.1–4.2 (1H, m), 4.2–4.4 (1H, m), 4.4–4.6 (1H, m), 6.9–7.1 (2H, m), 7.2–7.4 (8H, m).

f) To a solution of N-tert-butoxycarbonyl (5H-dibenzo[ a,d]cycloheptene) glycinol (1.49g, Example 1e) and 3,5-dimethylbenzyl bromide (0.92g) in 4ml DMF-THF (1:1) under nitrogen at 0° C. was added sodium hydride (130mg, 80% dispersion). The reaction was stirred at room temperature for 2h then partitioned between aqueous NH$_4$Cl-ethyl acetate. The organic phase was dried (MgSO$_4$) and solvent removed in vacuo. The residue was chromatographed on silica (5% ethyl acetate-petroleum ether eluant) to give N-tert-butoxycarbonyl (5H-dibenzo[ a,d]cycloheptene) glycinol-3,5-dimethylbenzyl ether. mp 116°–118° C. (petroleum ether). $^1$H NMR (360MHz, CDCl$_3$) 1.15 (9H, s), 2.36 (6H, s), 2.90–2.93 (1H, m), 3.18–3.21 (1H, m), 4.16– 4.37 (4H, m), 4.79–4.82 (1H, m), 6.88–6.94 (4H, m), 7.05–7.08 (1H, m), 7.21–7.32 (8H, m).

g) A solution of N-tert-butoxycarbonyl (5H-dibenzo[ a,d] cycloheptene) glycinol-3,5-dimethylbenzyl ether (0.55g, Example 1f) in 2ml dry CH$_2$Cl$_2$ was treated with trifluoroacetic acid (2ml) and stirred for 20 minutes. Solvent and other volatiles were removed in vacuo. The residue was dissolved in ethyl acetate, washed with aqueous Na$_2$CO$_3$, dried (MgSO$_4$) and solvent removed in vacuo. The residue was dissolved in ethanol and treated with oxalic acid to give the title compound. mp 175°–177° C. (ethanol-diethyl ether). $^1$H NMR (360MHz, DMSO-d$_6$) 2.27 (6H, s), 2.85–2.87 (1H, m), 3.17–3.19 (1H, m), 3.58–3.40 (1H, m), 4.15–4.40 (3H, m), 6.88 (2H, s), 6.92 (1H, s), 6.99–7.08 (2H, m), 7.28–7.48 (8H, m).

EXAMPLE 2

N-Acetamido-1-(5H-dibenzo[a,d]cyclohepten-5-yl)- 2-(3,5-dimethylbenzyloxy)ethylamine A solution of the product of Example 1 (0.35g) and acetic anhydride (0.178ml) in 3ml pyridine was allowed to stand overnight. The reaction was partitioned between ethyl acetate and 1N HCl. The organic phase was dried (MgSO$_4$) and solvent removed in vacuo. The residue was chromatographed (20% ethyl acetate-petroleum ether) to give the title compound. mp 115°–117° C. (ethyl acetate-petroleum ether). $^1$H NMR (360MHz, CDCl$_3$) 1.54 (6H, s), 2.34 (3H, s), 2.92–2.94 (1H, s), 3.19–3.23 (1H, m), 4.20–4.31 (3H, m), 4.65–4.8 (1H, m), 5.5–5.6 (1H, m), 6.90–6.96 (4H, m), 7.01–7.05 (1H, m), 7.21–7.34 (8H, m). Found: C, 81.3; H, 7.3; N, 3.2: Calculated for C$_{28}$H$_{29}$NO$_2$ C, 81.72; H, 7.10; N, 3.40%.

EXAMPLE 3

1-(10,11-Dihydro-5H-dibenzo[a,d]cyclohepten-5-yl]-2-(3,5-dimethylbenzyloxy)ethylamine, oxalate salt 5-Chlorodibenzosuberane was treated in an analogous manner to that described in Example 1 to yield the title compound. mp 197°–200° C. $^1$H NMR (360MHz,DMSO-d$_6$) δ 2.27 (6H, m), 2.8–3.1 (1H, br m), 3.15–3.25 (1H, m), 3.3–3.5 (3H, m), 4.1–4.2 (2H, m), 4.3–4.35 (1H, m), 4.4–4.5 (1H, m), 6.93 (3H, s), 7.1–7.3 (8H, m). Found: C, 71.83; H, 6.77; N, 2.97; Calculated for C$_{25}$H$_{29}$NO.C$_2$H$_2$O$_4$ C, 72.14; H, 6.95; N, 3.12%.

EXAMPLE 4

N-Acetamido-1-(10,11-dihydro-5H-dibenzo[a,d]cyclohepten-5-yl)-2-(3,5-dimethylbenzyloxy)ethylamine The product of Example 3 was acetylated in an analogous manner to that described in Example 2 to give the title compound. mp 109°–111° C. $^1$H NMR (360MHz, CDCl$_3$) δ 1.60 (3H, s), 2.35 (6H, s), 2.84–2.91 (2H, m), 3.37 (2H, s), 3.46–3.68 (2H, m), 4.14–4.17 (1H, m), 4.35–4.44 (2H, m), 4.84–4.90 (1H, m), 5.66–5.71 (1H, m), 6.98–7.25 (11H, m). Found: C, 71.83; H, 6.77; N, 2.97; Calculated for C$_{25}$H$_{29}$NO.C$_2$H$_2$O$_4$ C, 72.14; H, 6.95; N, 3.12%.

EXAMPLE 5

N,N-Dimethyl-1-(10,11-dihydro-5H-dibenzo[a,d]cyclohepten-5-yl)-2-(3,5-dimethylbenzyloxy)ethylamine, oxalate salt To a solution of the product of Example 3 (320mg) in 2ml methanol at 0° C. was added acetic acid (0.25ml) followed by sodium borohydride (0.1g) and aqueous formaldehyde (0.167ml of 37 wt %). Solvent was removed after 3 days and the residue purified by chromatography (1:1 ethyl acetate-petroleum ether eluant). The purified free base was dissolved in diethyl ether and oxalic acid in methanol was added. Solvent was removed to give the title compound. mp 68°–69° C. (ethyl acetate-petroleum ether). $^1$H NMR (360MHz, DMSO-d$_6$) 2.24 (6H, s), 2.49 (6H, s), 2.8–3.0 (2H, m), 3.32–3.50 (4H, m), 3.8–4.4 (4H, br m), 6.82 (2H, s), 6.88 (1H, s), 7.0–7.3 (8H, m). Found: C, 69.34; H, 6.71; N, 2.64: Calculated for C$_{28}$H$_{33}$NO.1.5 (C$_2$H$_2$O$_4$) C, 69.64; H, 6.78; N, 2.62%.

EXAMPLE 6

1-(10,11-Dihydro-5H-dibenzo[a,d]cyclohepten-5-yl)-2-(3,5-bistrifluoromethylbenzyloxy)ethyl amine, oxalate salt Prepared in an analogous manner to that described for the product of Example 3. mp 175°–176° C. $^1$H NMR (360MHz, DMSO-d$_6$) 2.8–3.0 (2H, m), 3.3–3.6 (3H, m), 4.1–4.3 (2H, m), 4.5–4.7 (2H, m), 7.0–7.4 (8H, m), 8.0–8.1 (3H, m).

EXAMPLE 7

N-Carbomethoxymethyl-1-(10,11-dihydro-5H-dibenzo[a,d]cyclohepten-5-yl)-2-(3,5-bistrifluoromethylbenzyloxy)ethylamine, oxalate salt A mixture of the title product of Example 6, methyl bromoacetate (one equivalent) and triethylamine (one equivalent) were refluxed in THF for 22h. The reaction was partitioned between diethyl ether-water and the organic phase separated and dried (MgSO$_4$). Solvent was removed in vacuo and the residue redissolved in ethanol. Oxalic acid was added, solvent removed in vacuo, and the residue recrystallised to give the title compound. mp 160°–165° C. (ethyl acetate-petroleum ether). $^1$H NMR (360MHz, DMSO-d$_6$) 2.8–3.0 (2H, m), 3.2 (2H, s), 3.4–3.5 (6H, m), 3.6–3.65 (1H, m), 3.9–3.95 (1H, m), 4.5 (3H, s), 7.00–7.2 (8H, m), 7.9 (3H, s).

EXAMPLE 8

N-Carbamoylmethyl-1-(10,11-dihydro-5H-dibenzo[a,d]cyclohepten-5-yl)-2-(3,5-bistrifluoromethylbenzyloxy)ethylamine, oxalate salt A solution of the product of Example 6 in 5ml methanol saturated with ammonia was sealed in a reaction vessel and left at 0° C. for 48h. Solvent was removed in vacuo, and the residue dissolved in ethanol. Oxalic acid and water were added to give the title compound. mp 120°–122° C. $^1$H NMR (360MHz, DMSO-d$_6$) 2.8–3.0 (2H, m), 3.3–3.7 (6H, m), 4.2–4.6 (4H, m), 7.00–7.4 (8H, m), 7.9 (1H, s), 7.95 (2H, s).,

EXAMPLE 9

3,5-Dimethylbenzyl-2-(9-fluoroenyl)glycinate a) A solution of N-(diphenylmethylene)glycine ethyl ester (5g) in tetrahydrofuran (15ml) was added dropwise to a cooled solution of lithium diisopropylamide (1 mol eq) in tetrahydrofuran (20ml) and hexane (11ml) at −70° C. After 1h at −70° C., a solution of 9-bromofluorene (4.58g) in tetrahydrofuxan (15ml) was added. After stirring the solution for 1h at −70° C. and then at room temperature (16h), the solution was diluted with saturated ammonium chloride solution (500ml) and diethyl ether (500ml). The organic phase was washed with saturated brine and dried (MgSO$_4$). After removal of the solvent in vacuo the residue was purified on a silica column to give ethyl N-(diphenylmethylene)-(9-fluoroenyl)glycinate, 2.2g.

b) The product of part (a) (2.2g) was heated at reflux for 16h with 5.5M-hydrochloric acid (30ml). The cooled solution was washed with diethyl ether and the aqueous phase evaporated to dryness. The residue was recrystallised from acetone-water to give 2-(9-fluorenyl)glycine hydrochloride, 0.7g.

c) To a solution of the product of part (b) (0.7g) and sodium carbonate (0.95g) in dioxan (5ml) and water (10ml) was added di-t-butyldicarbonate (0.664g). After stirring the solution for 16h at room temperature, water (50ml) and diethyl ether (60ml) were added. To the aqueous phase was added solid citric acid to pH 3 and the product extracted into ethyl acetate (3×30ml). The combined organic phases were washed with water, saturated brine, dried (MgSO$_4$) and evaporated to dryness to give N-t-butoxycarbonyl-2-(9-fluorenyl)glycine 0.75g.

d) To a solution of the product of part (c) (0.750g) in methanol (10ml) was added a solution of cesium carbonate (348mg) in water (5ml). The solvent was removed by evaporation and the residue dried by repeated evaporation from dimethylformamide (3×30ml). To the residue dissolved in dimethylformamide (50ml) was added 3,5-dimethylbenzyl bromide (0.636g) and the solution stirred at room temperature for 16h. The solvent was removed in vacuo and the residue partitioned between dichloromethane and water. The organic phase was washed with saturated brine, dried ($MgSO_4$) and evaporated in vacuo. The residue was chromatographed on silica gel eluting with mixtures of ethyl acetate in petroleum ether bp 60°–80° C. to give 3,5-dimethylbenzyl-N-t-butoxycarbonyl- 2-(9-fluorenyl)glycinate. Trifluoroacetic acid (3ml) was added to the ester (0.2g) and after 40 minutes the solvent was removed by evaporation and a solution of 4-toluenesulfonic acid (84mg) in ethanol (1ml) added to give 3,5-dimethylbenzyl-2-(9-fluorenyl)glycinate, 4-toluenesulphonic acid salt. mp 150°–151° C. Found: C, 70.19; H, 5.74; N, 2.61. $C_{24}H_{23}NO_2 \cdot C_7H_8SO_3$ requires C, 70.30; H, 5.90; N, 2.64%. m/z ($FAB^+$)=358 (M+H).

EXAMPLE 10

3,5-Dimethylbenzyl N-acetyl-2-(9-fluorenyl)glycinate 3,5-Dimethylbenzyl N-t-butoxycarbonyl-2-(9-fluorenyl)glycinate (Example 9d, 0.5g) was dissolved in trifluoroacetic acid (10ml) for 40 minutes then evaporated in vacuo. To a solution of the residue in pyridine (10ml) was added acetic anhydride (1ml) for 16h. The solvent was removed in vacuo and the residue crystallised from diethyl ether/petroleum ether bp 60°–80° C. to give the title compound mp 162°–164° C. Found: C, 78.19; H,. 6.26; N, 3.45. $C_{26}H_{25}NO_3$ requires C,. 78.17; H, 6.30; N, 3.50%. m/z ($CI^+$)=400 (M+H), ($CI^-$)=398 (M–H).

The following examples illustrate pharmaceutical compositions according to the invention.

EXAMPLE 11A Tablets containing 1–25mg of compound

|  | Amount mg | | |
| --- | --- | --- | --- |
| Compound of formula (I) | 1.0 | 2.0 | 25.0 |
| Microcrystalline cellulose | 20.0 | 20.0 | 20.0 |
| Modified food corn starch | 20.0 | 20.0 | 20.0 |
| Lactose | 58.5 | 57.5 | 34.5 |
| Magnesium Stearate | 0.5 | 0.5 | 0.5 |

EXAMPLE 11B Tablets containing 26–100mg of compound

|  | Amount mg | | |
| --- | --- | --- | --- |
| Compound of formula (I) | 26.0 | 50.0 | 100.0 |
| Microcrystalline cellulose | 80.0 | 80.0 | 80.0 |
| Modified food corn starch | 80.0 | 80.0 | 80.0 |
| Lactose | 213.5 | 189.5 | 139.5 |
| Magnesium Stearate | 0.5 | 0.5 | 0.5 |

The compound of formula (I), cellulose, lactose and a portion of the corn starch are mixed and granulated with 10% corn starch paste. The resulting granulation is sieved, dried and blended with the remainder of the corn starch and the magnesium stearate. The resulting granulation is then compressed into tablets containing 1.0mg, 2.0mg, 25.0mg, 26.0mg, 50.0mg and 100mg of the active compound per tablet.

EXAMPLE 12 Parenteral injection

|  | Amount mg |
| --- | --- |
| Compound of formula (I) | 1 to 100 mg |
| Citric Acid Monohydrate | 0.75 mg |
| Sodium Phosphate | 4.5 mg |
| Sodium Chloride | 9 mg |
| Water for injection | to 1 ml |

The sodium phosphate, citric acid monohydrate and sodium chloride are dissolved in a portion of the water. The compound of formula (I) is dissolved or suspended in the solution and made up to volume.

EXAMPLE 13 Topical formulation

|  | Amount mg |
| --- | --- |
| Compound of formula (I) | 1–10 mg |
| Emulsifying Wax | 30 g |
| Liquid paraffin | 20 g |
| White Soft Paraffin | to 100 g |

The white soft paraffin is heated until molten. The liquid paraffin and emulsifying wax are incorporated and stirred until dissolved. The compound of formula (I) is added and stirring continued until dispersed. The mixture is then cooled until solid.

SUBSTANCE P ANTAGONISM ASSAY

A. Receptor Expression in Monkey Kidney Cell Line (COS)

To express the cloned human neurokinin-1- receptor (NK1R) transiently in COS, the cDNA for the human NK1R was cloned into the expression vector pCDM9 which was derived from pCDM8 (INVITROGEN) by inserting the ampicillin resistance gene (nucleotide 1973 to 2964 from BLUESCRIPT SK+ (trademark, STRATAGENE, La Jolla, Calif., USA)) into the Sac II site. Transfection of 20 ug of the plasmid DNA into 10 million COS cells was achieved by electroporation in 800 µl of transfection buffer (135 mM NaCl, 1.2 mM $CaCl_2$, 1.2 mM $MgCl_2$, 2.4 mM $K_2HPO_4$, 0.6 mM $KH_2PO_4$, 10 mM glucose, 10 mM N-2-hydroxyethyl-piperazine-N' -2-ethane sulphonic acid (HEPES) pH 7.4) at 260 V and 950 µF using the IBI GENEZAPPER (trademark IBI, New Haven, Conn., USA). The cells were incubated in 10% fetal calf serum, 2 mM glutamine, 100U/ml penicillin-streptomycin, and 90% DMEM media (GIBCO, Grand Island, N.Y., USA) in 5% $CO_2$ at 37° C. for three days before the binding assay.

B. Stable Expression in Chinese Hamster Ovarian Cell Line

To establish a stable cell line expressing cloned human NK1R, the cDNA was subcloned into the vector pRcCMV (INVITROGEN). Transfection of 20 ug of the plasmid DNA into CHO cells was achieved by electroporation in 800 µl of transfection buffer supplemented with 0.625 mg/ml Herring sperm DNA at 300 V and 950 µF using the IBI GENEZAPPER (IBI). The transfected cells were incubated in CHO media [10% fetal calf serum, 100 U/ml penicillin-streptomycin, 2 mM glutamine, 1/500 hypoxanthine-thymidine (ATCC), 90% IMDM media (JRH BIOSCIENCES, Lenexa, Kans., USA), 0.7 mg/ml G418 (GIBCO)] in 5% $CO_2$ at 37° C. until colonies were visible. Each colony was separated and propagated. The cell clone with the highest number of human NK1R was selected for subsequent applications such as drug screening.

C. Assay Protocol using COS or CHO

The binding assay of human NK1R expressed in either COS or CHO cells is based on the use of $^{125}$I-substance P ($^{125}$I-SP, from DU PONT, Boston, Mass.) as a radioactively labeled ligand which competes with unlabeled substance P or any other ligand for binding to the human NK1R. Monolayer cell cultures of COS or CHO were dissociated by the non-enzymatic solution (SPECIALTY MEDIA, Lavellette, N.J.) and resuspended in appropriate volume of the binding buffer (50 mM Tris pH 7.5, 5 mM $MnCl_2$, 150 mM NaCl, 0.04 mg/ml bacitracin, 0.004 mg/ml leupeptin, 0.2 mg/ml BSA, 0.01 mM phosphoramidon) such that 200 µl of the cell suspension would give rise to about 10,000 cpm of specific $^{125}$I-SP binding (approximately 50,000 to 200,000 cells). In the binding assay, 200 ul of cells were added to a tube containing 20 ul of 1.5 to 2.5 nM of $^{125}$I-SP and 20 µl of unlabeled substance P or any other test compound. The tubes were incubated at 4° C. or at room temperature for 1 hour with gentle shaking. The bound radioactivity was separated from unbound radioactivity by GF/C filter (BRANDEL, Gaithersburg, Md.) which was prewetted with 0.1% polyethylenimine. The filter was washed with 3 ml of wash buffer (50 mM Tris pH 7.5, 5 mM $MnCl_2$, 150 mM NaCl) three times and its radioactivity was determined by gamma counter.

The activation of phospholiphase C by NK1R may also be measured in CHO cells expressing the human NK1R by determining the accumulation of inositol monophosphate which is a degradation product of $IP_3$. CHO cells are seeded in 12-well plate at 250,000 cells per well. After incubating in CHO media for 4 days, cells are loaded with 5 µCi of $^3$H-myoinositol in 1 ml of media per well by overnight incubation. The extracellular radioactivity is removed by washing with phosphate buffered saline. LiCl is added to the well at final concentration of 10 mM with or without the test compound, and incubation is continued at 37° C. for 15 min. Substance P is added to the well at final concentration of 0.3nM to activate the human NK1R. After 30 min of incubation at 37° C., the medium is removed and 0.1N HCl is added. Each well is sonicated at 4° C. and extracted with $CHCl_3$/methanol (1:1). The aqueous phase is applied to a 1 ml Dowex AG 1×8 ion exchange column. The column is washed with 0.1N formic acid followed by 0.025M ammonium formate-0.1N formic acid. The inositol monophosphate is eluted with 0.2M ammonium formate-0.1N formic acid and quantitated by beta counter.

The data in Table 1 were obtained for compounds of formula (I):

TABLE 1

| SUBSTANCE P ANTAGONISM RESULTS | |
| --- | --- |
| Compound of Ex # | $IC_{50}$ @ NK1R (nM) |
| 1 | 80 |
| 2 | 70 |
| 3 | 100, 190 |
| 4 | 150 |
| 5 | 320 |
| 6 | 250 |
| 7 | 42% @ 1 µM |
| 8 | 60 |
| 9 | 300 |
| 10 | 300 |

We claim:

1. A compound of formula (I), or a salt or prodrug thereof:

$$Q-\underset{NR^1R^2}{\overset{R^3}{C}}-\underset{Z}{\overset{X\ Y\ R^4}{C-C}}-R^5 \qquad (I)$$

wherein

Q represents a group

[structure: two phenyl rings bridged by CH and W, with $(R^7)_m$ on left ring and $(R^8)_n$ on right ring]

where W represents a bond, O, S, —CH$_2$CH$_2$—, —CH=CH— or a group NR$^6$, where R$^6$ is H or C$_{1-6}$alkyl and one or both of the phenyl rings may be replaced by a heteroaryl moiety;

X and Y each represent H or X and Y together form a group =O;

Z represents O, S or NR$^8$, where R$^8$ represents H or C$_{1-6}$alkyl;

R$^1$ and R$^2$ independently represent H; C$_{1-6}$ alkyl optionally substituted by hydroxy, cyano, COR$^a$, COOR$^a$, CONR$^a$R$^b$, COC$_{1-4}$alkylNR$^a$R$^b$, CONR$^a$C$_{1-4}$alkyl-CONR$^a$R$^b$ or NR$^a$R$^b$, (where R$^a$ and R$^b$ each independently represent H, C$_{1-6}$ alkyl, phenyl (optionally substituted by one or more of C$_{1-6}$alkyl, C$_{1-6}$alkoxy, halo and trifluoromethyl) or phenyl(C$_{1-4}$alkyl) (optionally substituted in the phenyl ring by one or more of C$_{1-6}$ alkyl, C$_{1-6}$ alkoxy, halo and trifluoromethyl)); phenyl(C$_{1-4}$ alkyl), (optionally substituted by one or more of C$_{1-6}$ alkyl, C$_{1-6}$ alkoxy, halo and trifluoromethyl in the phenyl ring); C$_{2-6}$ alkylene; COC$_{1-6}$alkylhalo; COR$^a$; COOR$^a$; CONHR$^a$; COC$_{1-4}$alkylNR$^a$R$^b$; or CONR$^a$C$_{1-4}$alkylCONR$^a$R$^b$; (where R$^a$ and R$^b$ are as previously defined) or R$^1$ and R$^2$ together form a chain (CH$_2$)$_p$ where p is 4 or 5 and where one non-terminal methylene group may optionally be replaced by an oxygen atom or a group NR$^x$, where R$^x$ is H or C$_{1-6}$ alkyl;

R$^3$ represents H or C$_{1-6}$alkyl;

R$^4$ represents H, C$_{1-6}$ alkyl or phenyl (optionally substituted by one or more of C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ each independently represent H, C$_{1-6}$ alkyl, phenyl or trifluoromethyl);

R$^5$ represents (CH$_2$)$_q$phenyl, wherein q is 0, 1, 2 or 3 which may optionally be substituted in the phenyl ring by one or more of C$_{1-6}$ alkyl, C$_{2-6}$ alkenyl, C$_{2-6}$ alkynyl, halo, cyano, nitro, trifluoromethyl, trimethylsilyl, , SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ are as above defined;

each R$^7$ and R$^8$ independently represents C$_{1-6}$ alkyl, C$_{2-6}$ alkenyl, C$_{2-6}$ alkynyl, halo, cyano, nitro, trifluoromethyl, trimethylsilyl, SR$^c$, SOR$^c$, SO$_2$R$^c$, OR$^c$, NR$^c$R$^d$, NR$^c$COR$^d$, NR$^c$COOR$^d$, COOR$^c$ or CONR$^c$R$^d$, where R$^c$ and R$^d$ are as above defined; and m and n independently represent 0, 1, 2, 3 or 4.

2. A compound as claimed in claim 1 wherein Q represents a group

[structure: two phenyl rings bridged by CH and W$^1$]

where W$^1$ is a bond, O, S or a group NR$^6$, where R$^6$ is H or C$_{1-6}$ alkyl;

$R^1$ and $R^2$ each independently represent H, $C_{1-6}$ alkyl, phenyl($C_{1-4}$ alkyl), $COR^{10}$, $COOR^{10}$ or $CONHR^{10}$, where $R^{10}$ is $C_{1-6}$ alkyl or phenyl;

$R^4$ represents H, $C_{1-6}$ alkyl or phenyl (optionally substituted by one or more of $C_{1-6}$ alkyl, $C_{2-6}$ alkenyl, $C_{2-6}$ alkynyl, halo, cyano, nitro, trifluoromethyl, $SCH_3$, $SOCH_3$, $SO_2CH_3$, $OR^c$, $NR^cR^d$, $NR^cCOR^d$, $NR^cCOOR^d$, $COOR^c$ or $CONR^cR^d$ (where $R^c$ and $R^d$ are as above defined); and $R^5$ represents $(CH_2)_q$phenyl, wherein q is 0, 1, 2 or 3 which may optionally be substituted by one or more of $C_{1-6}$ alkyl, $C_{2-6}$ alkenyl, $C_{2-6}$ alkynyl, halo, cyano, nitro, trifluoromethyl, $SCH_3$, $SOCH_3$, $SO_2CH_3$, $OR^c$, $NR^cR^d$, $NR^cCOR^d$, $NR^cCOOR^d$, $COOR^c$ or $CONR^cR^d$ (where $R^c$ and $R^d$ are as above defined);

wherein any phenyl (including benzyl) ring in the definitions of $R^1$ or $R^2$ (including $R^{10}$) above may be optionally substituted by one or more of $C_{1-6}$ alkyl, $C_{1-6}$ alkoxy, halo or trifluoromethyl.

3. A compound as claimed in claim 1 wherein W represents a bond.

4. A compound as claimed in claim 1 wherein W represents $CH_2CH_2$ or $HC=CH$.

5. A compound as claimed in claim 1 wherein X and Y each represent H and Z represents O.

6. A compound as claimed in claim 1 wherein $R^4$ is H and $R^5$ is substituted phenyl.

7. A compound as claimed in claim 1 selected from:
1-(5H-dibenzo[a,d]cyclohepten-5-yl)-2-(3,5-dimethylbenzyloxy)ethylamine;
N-acetamido-1-(5H-dibenzo[a,d]cyclohepten-5-yl)-2-(3,5-dimethylbenzyloxy)ethylamine;
1-(10,11-dihydro-5H-dibenzo[a,d]cyclohepten-5-yl)-2-(3,5-dimethylbenzyloxy)ethylamine;
N-acetamido-1-(10,11-dihydro-5H-dibenzo[a,d]cyclohepten- 5-yl)-2-(3,5-dimethylbenzyloxy)ethylamine;
N,N-dimethyl-1-(10,11-dihydro-5H-dibenzo[a,d]cyclohepten- 5-yl)-2-(3,5-dimethylbenzyloxy)ethylamine;
1-(10,11-dihydro-5H-dibenzo[a,d]cyclohepten-5-yl)-2-(3,5-bistrifluoromethylbenzyloxy)ethylamine;
N-carbomethoxymethyl-1-(10,11-dihydro-5H-dibenzo[a,d]cyclohepten-5-yl)-2-(3,5-bistrifluoromethylbenzyloxy)ethylamine;
N-carbamoylmethyl-1-(10,11-dihydro-5H-dibenzo[a,d]cyclohepten-5-yl)-2-(3,5-bistrifluoromethylbenzyloxy)ethylamine;
3,5-dimethylbenzyl-2-(9-fluorenyl)glycinate;
3,5-dimethylbenzyl N-acetyl-2-(9-fluorenyl)glycinate;
and salts and prodrugs thereof.

8. A pharmaceutical composition comprising a compound as claimed in claim 1 in association with a pharmaceutically acceptable carrier or excipient.

9. A method for the treatment of a physiological disorder associated with an excess of tachykinins, which method comprises administration to a patient in need thereof of a tachykinin-reducing amount of a compound according to claim 1.

10. A method according to claim 9 for the treatment of pain or inflammation.

11. A method according to claim 9 for the treatment of migraine.

12. A method according to claim 9 for the treatment or prevention of postherpetic neuralgia.

* * * * *